United States Patent [19]

Lorenzoni et al.

[11] Patent Number: 5,788,818
[45] Date of Patent: Aug. 4, 1998

[54] PROCESS FOR THE PURIFICATION OF ACETONE

[75] Inventors: Lorenzo Lorenzoni, Porto Torres; Salvatore Simula, Ittiri; Giuseppe Messina, Alghero; Riccardo Mansani, Sassari, all of Italy

[73] Assignee: Enichem S.p.A., Milano, Italy

[21] Appl. No.: 714,358

[22] Filed: Sep. 16, 1996

[30] Foreign Application Priority Data

Oct. 6, 1995 [IT] Italy ................... MI95A2032

[51] Int. Cl.$^6$ .................. B01D 3/34; C07C 45/82
[52] U.S. Cl. .................. 203/17; 203/37; 203/64; 203/82; 203/84; 568/411
[58] Field of Search .................. 203/81–82, 17, 203/64, 37, 14, 84; 568/411

[56] References Cited

U.S. PATENT DOCUMENTS

| | | | |
|---|---|---|---|
| 2,737,480 | 3/1956 | Adams et al. | 568/411 |
| 3,405,038 | 10/1968 | Kohmoto | 203/69 |
| 3,668,256 | 6/1972 | Brundege | 568/411 |
| 4,160,111 | 7/1979 | Strahorn | 568/749 |
| 4,329,510 | 5/1982 | Uno et al. | 568/411 |
| 4,336,109 | 6/1982 | Hosaka et al. | 203/37 |
| 4,351,967 | 9/1982 | Nishimura et al. | 203/64 |
| 4,559,110 | 12/1985 | Swearingen et al. | 203/17 |
| 4,626,600 | 12/1986 | Fulmer et al. | 568/411 |
| 4,722,769 | 2/1988 | Chan et al. | 203/37 |
| 5,567,853 | 10/1996 | Gupta | 568/411 |

FOREIGN PATENT DOCUMENTS 554500 1/1960 Belgium .
0 040 985 12/1981 European Pat. Off. .
0 242 555 10/1987 European Pat. Off. .

*Primary Examiner*—Virginia Manoharan
*Attorney, Agent, or Firm*—Oblon, Spivak, McClelland, Maier & Neustadt, P.C.

[57] ABSTRACT

A process for the purification of raw acetone deriving from processes for the production of phenol acetone, impurity mainly due to cumene, water, aldehydes and methanol, the steps of:

- feeding the stream of raw acetone coming from the primary fractionation of a plant for the production of phenol and acetone to a first distillation column to which a solution of sodium hydroxide at 2% is also fed;
- sending the stream at the head of the first column, containing of acetone, water and cumene to a second column to which the extractive solvent triethyleneglycol is also fed;
- recovering substantially anhydrous acetone from the head of the second column;
- feeding the bottom product of the second column, containing triethyleneglycol, water, cumene and acetone to a third distillation column in which an azeotropic mixture of water and cumene is recovered from the head and anhydrous triethyleneglycol from the bottom;
- sending the azeotropic mixture of water and cumene to a decanter in which a water phase is separated, containing acetone, which is recycled to the first column and an organic phase, containing cumene and acetone, which is sent to the primary fractionation.

8 Claims, 3 Drawing Sheets

PROCESS FOR THE PURIFICATION OF ACETONE

The present invention relates to a process for the purification of acetone contained in a stream of raw acetone coming from processes for the production of phenol-acetone.

In present-day plants for the production of phenol-acetone a stream of cumene is subjected to oxidation with air in a slightly alkaline environment. The cumylhydroperoxide thus obtained is subsequently hydrolyzed, in the presence of sulfuric acid, to give a mixture of phenol and acetone from which a stream of raw acetone is separated by rectification. The known purification of acetone is carried out according to the scheme shown in FIG. 1.

In practice, the stream of raw acetone, impure mainly for cumene, water, aldehydes and methanol, coming from the head of the primary fractionator is distilled on a line of one or more columns in series, for a total of 70 plates, subjected to pressures of between 350 and 500 tors and reflux ratios of between 3.5 and 4.5.

The raw acetone (1) is fed to the first plate of column A" or to the tenth if only one column with 70 plates is used. The product within specification containing a quantity of water of about 0.2% and about 300 ppm of methanol (2) is recovered from the head of A". A solution at 14% of sodium hydroxide (3) is fed to the 26° plate of the same column, which has the function of neutralizing the acidity and inducing the condensation of the aldehyde impurities present in the raw product. The presence of water in the feeding, in a quantity of not less than 15% is, moreover, necessary to prevent the fouling of the columns due to the formation of sodic salts. The cumene (4) tends to accumulate on the bottom of column A" from which it is eliminated together with substantial quantities of acetone. The bottom product of column A" (5) containing water, polyaldehydes, methanol and acetone is fed to column A'. The polyaldehydes, formed by the effect of sodium hydroxide, are eliminated from the bottom of column A' together with most of the water (6), whereas the stream at the head (7), containing acetone, is refed to column A".

For the correct functioning of this column it is necessary to minimize the quantity of cumene in the feeding, which is achieved by maintaining a high reflux ratio in the primary fractionator (separation of raw acetone from raw phenol).

In the stream of raw acetone (1) water represents the critical impurity in that, as it forms an azeotropic mixture with acetone (acetone 95.6%, b.p. 54.5° C.), it cannot be removed by fractional distillation. The problem is resolved, in commercial purification processes of acetone, by carrying out the distillation at reduced pressure. It is thus possible to vary the composition of the azeotropic mixture by reducing the content of water to an acceptable level.

This procedure however has disadvantages such as, for example, a high consumption of energy due to the activity of the pumps and the necessity of operating with high reflux ratios.

A purification process has now been found which enables the production of a much higher-quality acetone than that obtained with the processes used so far, and which also allows considerable energy-saving.

In particular the process of the present invention is based on the use of an extractive distillation with triethyleneglycol (TEG), at atmospheric pressure, as an alternative to distillations at reduced pressure, to separate the water/acetone azeotropic mixture.

In accordance with this, the present invention relates to a process for the purification of raw acetone coming from processes for the production of phenol-acetone impure mainly because of the presence of cumene, water, aldehydes and methanol which comprises:

feeding the stream of raw acetone coming from the primary fractionation of a plant for the production of phenol/acetone to a first distillation column to which a solution of sodium hydroxide at 2% is also fed;

sending the stream at the head of the first column, consisting of acetone, water and cumene to a second column to which the extractive solvent triethyleneglycol is also fed;

recovering the practically anhydrous acetone from the head of the second column;

feeding the bottom product of the second column, containing triethyleneglycol, water, cumene and acetone to a third distillation column in which an azeotropic mixture of water/cumene is recovered from the head and anhydrous triethyleneglycol from the tail;

sending the azeotropic mixture of water/cumene to a decanter in which a water phase is separated, containing acetone, which is recycled to the first column and an organic phase, containing cumene and acetone, which is sent to the primary fractionation.

The process of the present invention in addition to allowing the production of a leading quality acetone (content of water <300 ppm and methanol <100 ppm) without relevant increases in production costs, provides the following advantages with respect to the processes used at present:

the possibility of operating at atmospheric pressure, thus avoiding the use of vacuum pumps with consequent energy saving, reductions in emissions and the possibility of increasing the capacity;

energy saving deriving from the reduction in the reflux ratios in the purification phase with further possibilities of increasing the capacity;

energy saving deriving from the reduction of the reflux ratio in the primary fractionation.

In the proposed process, in fact, a key role is played by the formation of the azeotropic mixture of water/cumene which is easily separated at the head of the third column.

The presence of a certain quantity of cumene in the raw acetone is therefore tolerable and reduces the severity of the primary fractionation by lowering the reflux ratios.

BRIEF DESCRIPTION OF THE DRAWINGS

The known purification of acetone is carried out according to the scheme shown in FIG. 1.

The purification of acetone according to the present invention is carried out according to the schemes of FIGS. 2 and 3.

DESCRIPTION OF THE PREFERRED EMBODIMENTS

Figure 1:
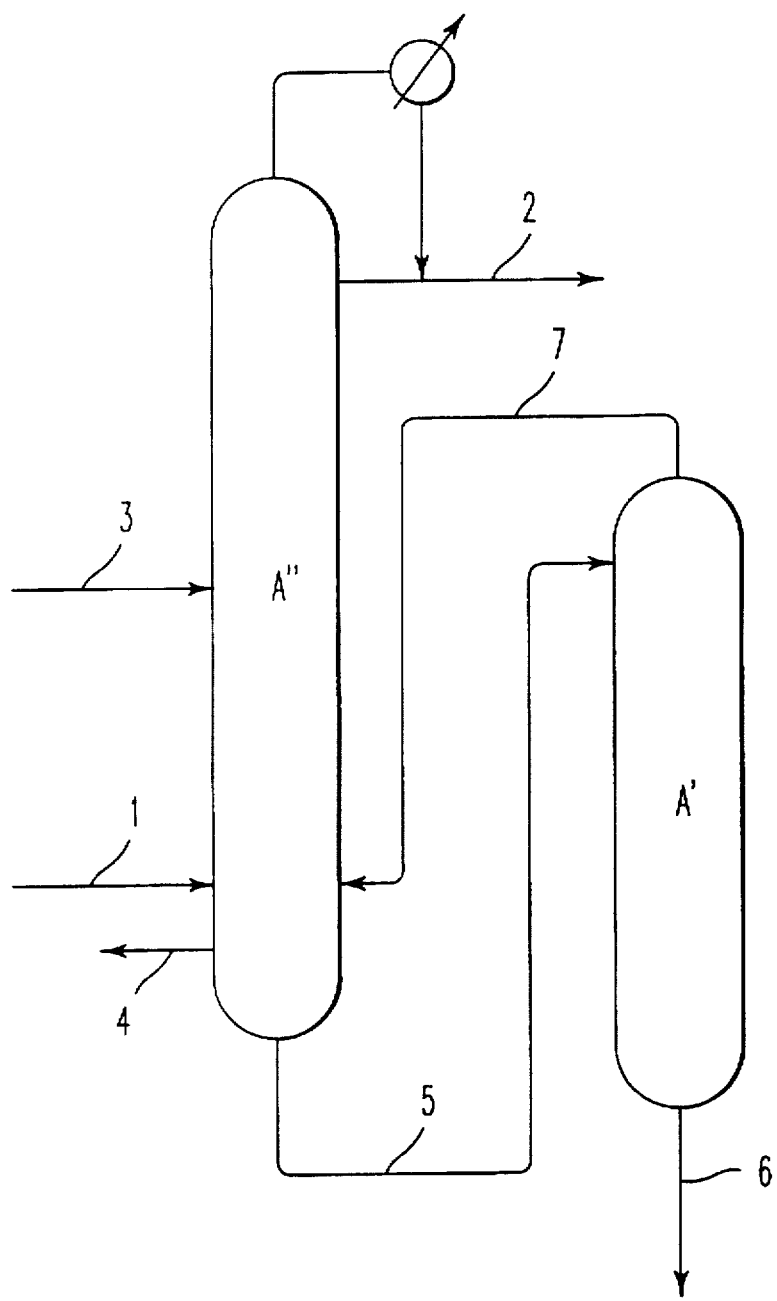
Figure 2:
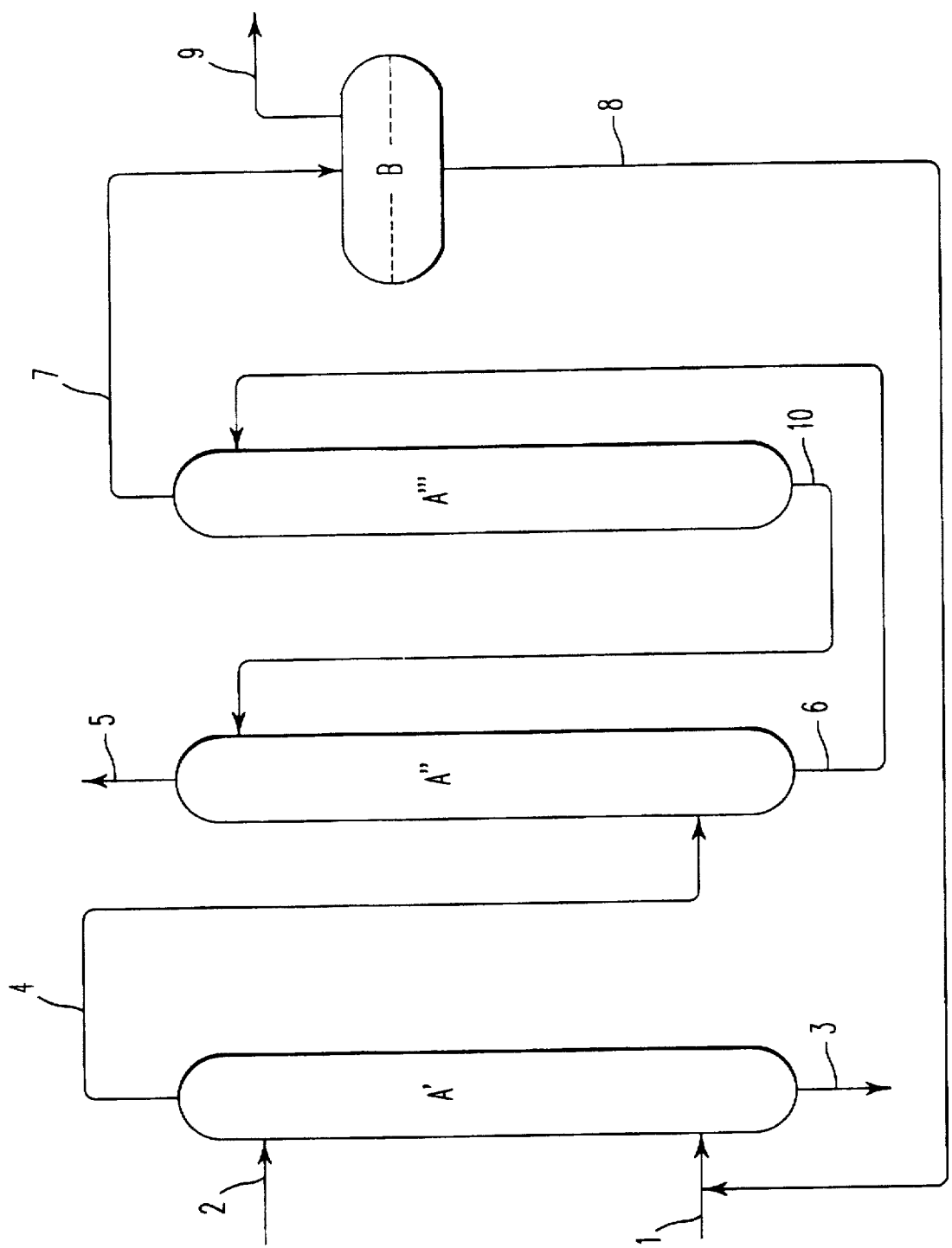

The scheme necessary for carrying out the purification of the invention is represented in FIG. 2 of which the main aspects are described hereunder.

The stream of raw acetone (1) coming from the primary fractionation is fed to the 3°–10° plate (theoretical plates, counting upwards), preferably to the 6°, of a column (A') consisting of a total number of plates of between 16–26, preferably 20. The column operates at atmospheric pressure, with a reflux ratio of between 0.2 and 0.5, preferably 0.3 and a temperature at the tail varying from 102° to 110° C. depending on its pressure drop. A quantity of between 12% and 17%, preferably 15%, with respect to raw acetone of a solution of sodium hydroxide at 2% (2) is fed to the 13°–23° plate, preferably the 19°, of the same column. The aldehydes (in the form of polyaldehydes), most of the water fed with the soda and part of the methanol (3) are eliminated from the tail of this column. The separation of the methanol can be improved with a greater quantity of water which, when fed as a solution of sodium hydroxide, in countercurrent to the raw product, has the effect of withholding most of this impurity on the bottom of the column.

The stream (4) coming from the head of column A' is then fed to the 3°–10° plate, preferably the 6°, of column A", which consists of a total number of plates of between 23–36, preferably 32, and operates at atmospheric pressure, with a reflux ratio of between 0.4 and 1.5, preferably 1 and an autogenous temperature at the tail, typically of 120° C., determined by the temperature at the tail of column A'".

In this column the feeding is put in contact at the 25°–40° plate, with the extractive solvent triethyleneglycol, in a quantity equal to 0.6 to 1 times the raw product fed to column A', by whose effect the azeotropic mixture of water-acetone is separated and the water withheld on the bottom of the column. A practically anhydrous acetone (content of water <300 ppm) is recovered from the head (5). The bottom product of column A", containing TEG, water, cumene and a quantity of acetone typically of about 3%, is fed to the 6°–19° plate, preferably the 13°, of column A'" for the recovery of the extractive solvent.

The formation of the azeotropic mixture of water/cumene (b.p. 95° C., Cumene 56%) for the dehydration of the TEG is exploited in this column, which can consist of a number of plates of between 9–20, preferably 15, and operates at atmospheric pressure, at a reflux ratio of between 0.1 and 0.7, preferably 0.2, with respect to the raw product fed to column A'.

The azeotropic mixture, recovered at the head (7), is collected in a decanter (B) where the two phases are separated. The water phase, containing up to 33% of acetone, is recycled to column A' (8). The organic phase, containing up to 33% of Cumene and up to 21% of acetone (9), is recycled to the primary fractionation.

The anhydrous TEG (10) is recovered from the tail of column A'", and is recycled to column A".

EXAMPLE 1

Figure 3:
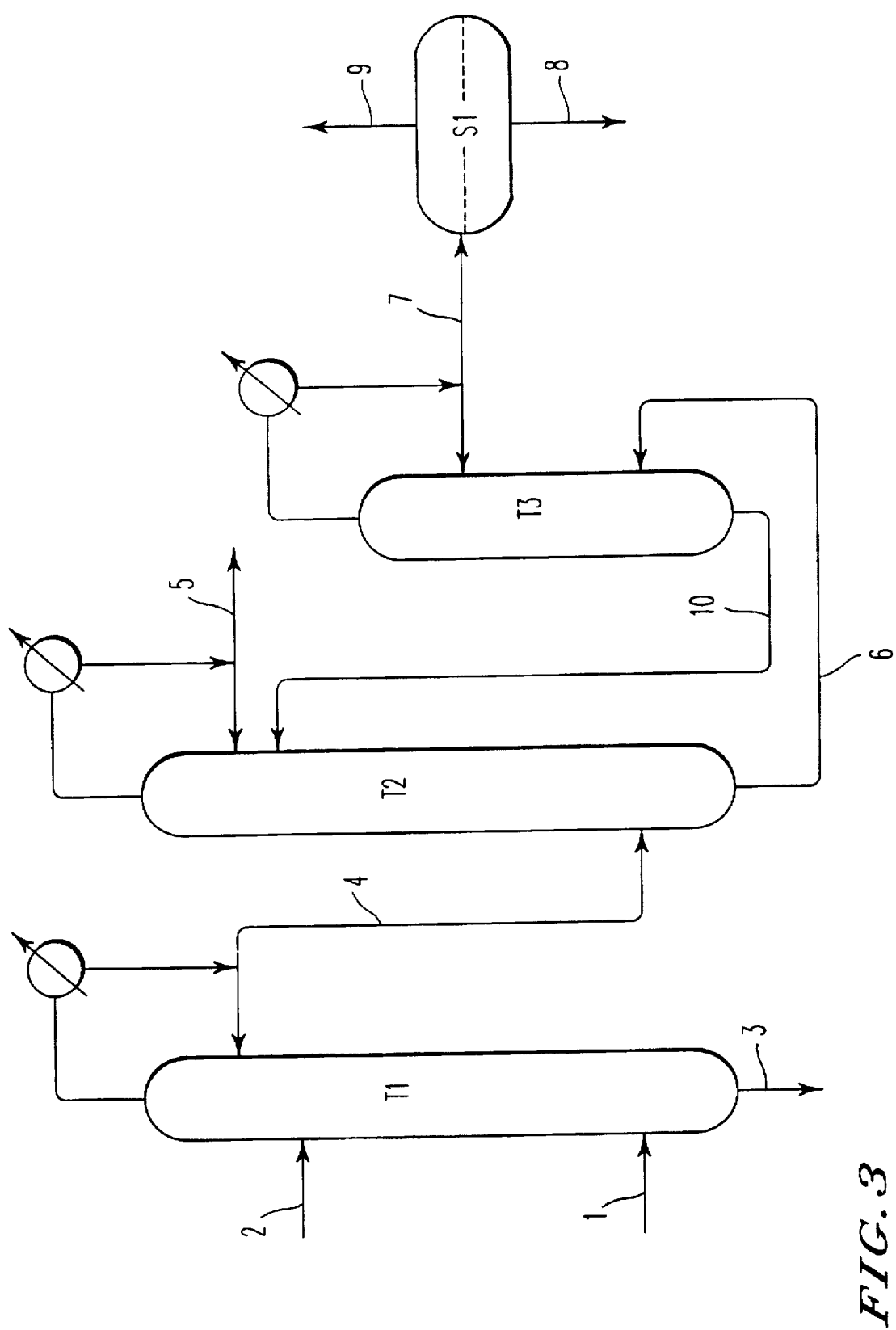

The test is carried out in a "bench scale" apparatus like that shown in FIG. 3, consisting of a line of three columns in series and a phase separator S1.

Column T1 consists of 30 plates, T2 of 45 plates and T3 of 15 plates. The plates are perforated, made of glass, with a diameter of 50 mm, supplied by NORMSCHLIFT, efficiency: 65% at total reflux temperature.

The stream of raw acetone (1) coming from primary fractionation is fed to the 12° plate of column T1. The solution of sodium hydroxide at 2% (2) is fed to the 30° plate of the same column. The aldehydes (in the form of polyaldehydes), most of the water fed with the sodium carbonate and part of the methanol (3) are eliminated from the tail of this column.

The stream (4) coming from the head of column T1 is then fed to the 8° plate of column T2. The recycled triethyleneglycol (10) is also fed to the 25° plate of this column. A practically anhydrous acetone (5) is recovered from the head of T2 whereas a stream containing TEG, water, cumene and acetone (6) is recovered from the tail. This stream is fed to the 10° plate of column T3 for the recovery of the extractive solvent.

The azeotropic mixture, recovered at the head (7), is collected in this column in a decanter S1 where the two phases are separated: a water phase, containing acetone (8), which is recycled to column T1; an organic phase, containing cumene and acetone (9). The anhydrous TEG (10) is recovered from the tail of column T3 and is recycled to column T2.

| Operating parameters | | |
|---|---|---|
| Feeding column T1 | | |
| stream of raw acetone | | 3042 cc/h |
| (H$_2$O 2.5%; cumene 150 ppm; methanol 210 ppm) | | |
| water phase from S1 | | 104 cc/h |
| H$_2$O make up | | — |
| NaOH (2%) | | 458 cc/h |
| Run parameters | | |
| Temperatures | | |
| Tail T1 104° C. | Reflux T1 | 586 cc/h |
| Head T1 62° C. | Reflux T2 | 3000 cc/h |
| Tail T2 112° C. | Reflux T3 | 480 cc/h |
| Tail T3 183° C. | Recycled TEG | 1430 cc/h |
| Head T3 106° C. | Pressure | 1 atm |
| Significant analyses | | |
| Acetone tail T1 | | 60 ppm |
| Acetone tail T2 | | 2.3% |
| Acetone organic phase S1 | | 10.7% |
| Acetone water phase S1 | | 18.5% |
| H$_2$O tail T2 | | 9.9% |
| Cumene tail T2 | | 11.1% |
| Cumene tail T3 | | 12.7% |
| Characteristics of end product | | |
| Content of H$_2$O | | 800 ppm |
| Content of methanol | | 150 ppm |
| Permanganate test ASTM D1363 | | 12 h |

EXAMPLE 2

The procedure is carried out as described in example 1, with the following operating parameters:

| Feeding column T1 | | |
|---|---|---|
| stream of raw acetone | | 3028 cc/h |
| (H$_2$O 2.5%; cumene 150 ppm; methanol 210 ppm) | | |
| water phase from S1 | | 133 cc/h |
| H$_2$O make up | | 736 cc/h |
| NaOH (2%) | | 467 cc/h |
| Run parameters | | |
| Temperatures | | |
| Tail T1 105° C. | Reflux T1 | 1123 cc/h |
| Head T1 60° C. | Reflux T2 | 3001 cc/h |
| Tail T2 120° C. | Reflux T3 | 520 cc/h |
| Tail T3 182° C. | Recycled TEG | 1430 cc/h |
| Head T3 110° C. | Pressure | 1 atm |
| Significant analyses | | |
| Acetone tail T1 | | 451 ppm |
| Acetone tail T2 | | 1.6% |
| Acetone organic phase S1 | | 12.0% |
| Acetone water phase S1 | | 21.9% |
| H$_2$O tail T2 | | 5.9% |
| Cumene tail T2 | | 10.8% |
| Cumene tail T3 | | 11.7% |
| Characteristics of end product | | |
| Content of H$_2$O | | 600 ppm |
| Content of methanol | | 60 ppm |
| Permanganate test (ASTM D1363) | | 20 h |

EXAMPLE 3

The procedure is carried out as described in example 1, with the following operating parameters:

Feeding column T1

| | |
|---|---|
| stream of raw acetone | 3033 cc/h |
| ($H_2O$ 2.5%; cumene 150 ppm; methanol 210 ppm) | |
| water phase from S1 | 130 cc/h |
| $H_2O$ make up | 745 cc/h |
| NaOH (2%) | 467 cc/h |

Run parameters

Temperatures

| | | | |
|---|---|---|---|
| Tail T1 105° C. | Reflux T1 | 1115 cc/h | |
| Head T1 60° C. | Reflux T2 | 3000 cc/h | |
| Tail T2 122° C. | Reflux T3 | 510 cc/h | |
| Tail T3 184° C. | Recycled TEG | 1760 cc/h | |
| Head T3 110° C. | Pressure | 1 atm | |

Significant analyses

| | |
|---|---|
| Acetone tail T1 | 400 ppm |
| Acetone tail T2 | 1.3% |
| Acetone organic phase S1 | 13.7% |
| Acetone water phase S1 | 21.6% |
| $H_2O$ tail T2 | 4.9% |
| Cumene tail T2 | 11.0% |
| Cumene tail T3 | 11.8% |

Characteristics of end product

| | |
|---|---|
| Content of $H_2O$ | 307 ppm |
| Content of methanol | 57 ppm |
| Permanganate test (ASTM D1363) | 15 h |

EXAMPLE 4

The procedure is carried out as described in example 1, with the following operating parameters:

Feeding column T1

| | |
|---|---|
| stream of raw acetone | 3045 cc/h |
| ($H_2O$ 2.5%; cumene 150 ppm; methanol 210 ppm) | |
| water phase from S1 | 137 cc/h |
| $H_2O$ make up | 730 cc/h |
| NaOH (2%) | 467 cc/h |

Run parameters

Temperatures

| | | | |
|---|---|---|---|
| Tail T1 105° C. | Reflux T1 | 1117 cc/h | |
| Head T1 61° C. | Reflux T2 | 4000 cc/h | |
| Tail T2 123° C. | Reflux T3 | 518 cc/h | |
| Tail T3 183° C. | Recycled TEG | 1760 cc/h | |
| Head T3 111° C. | Pressure | 1 atm | |

Significant analyses

| | |
|---|---|
| Acetone tail T1 | 432 ppm |
| Acetone tail T2 | 1.1% |
| Acetone organic phase S1 | 12.2% |
| Acetone water phase S1 | 19.3% |
| $H_2O$ tail T2 | 5.0% |
| Cumene tail T2 | 11.0% |
| Cumene tail T3 | 11.6% |

Characteristics of end product

| | |
|---|---|
| Content of $H_2O$ | 230 ppm |
| Content of methanol | 61 ppm |
| Permanganate test (ASTM D1363) | 13 h |

EXAMPLE 5

The procedure is carried out as described in example 1, with the following operating parameters:

Feeding column T1

| | |
|---|---|
| stream of raw acetone | 3030 cc/h |
| ($H_2O$ 2.5%; cumene 150 ppm; methanol 210 ppm) | |
| water phase from S1 | 133 cc/h |
| $H_2O$ make up | 741 cc/h |
| NaOH (2%) | 467 cc/h |

Run parameters

Temperatures

| | | | |
|---|---|---|---|
| Tail T1 104° C. | Reflux T1 | 1160 cc/h | |
| Head T1 60° C. | Reflux T2 | 3010 cc/h | |
| Tail T2 120° C. | Reflux T3 | 520 cc/h | |
| Tail T3 183° C. | Recycled TEG | 1760 cc/h | |
| Head T3 113° C. | Pressure | 1 atm | |

Significant analyses

| | |
|---|---|
| Acetone tail T1 | 360 ppm |
| Acetone tail T2 | 1.2% |
| Acetone organic phase S1 | 15.0% |
| Acetone water phase S1 | 22.0% |
| $H_2O$ tail T2 | 5.1% |
| Cumene tail T2 | 12.8% |
| Cumene tail T3 | 12.7% |

Characteristics of end product

| | |
|---|---|
| Content of $H_2O$ | 309 ppm |
| Content of methanol | 63 ppm |
| Permanganate test (ASTM D1363) | 12 h |

EXAMPLE 6

The procedure is carried out as described in example 1, with the following operating parameters:

Feeding column T1

| | |
|---|---|
| stream of raw acetone | 3031 cc/h |
| ($H_2O$ 2.5%; cumene 150 ppm; methanol 210 ppm) | |
| water phase from S1 | 132 cc/h |
| $H_2O$ make up | 735 cc/h |
| NaOH (2%) | 467 cc/h |

Run parameters

Temperatures

| | | | |
|---|---|---|---|
| Tail T1 105° C. | Reflux T1 | 1160 cc/h | |
| Head T1 60° C. | Reflux T2 | 4000 cc/h | |
| Tail T2 123° C. | Reflux T3 | 529 cc/h | |
| Tail T3 184° C. | Recycled TEG | 1760 cc/h | |
| Head T3 113° C. | Pressure | 1 atm | |

Significant analyses

| | |
|---|---|
| Acetone tail T1 | 250 ppm |
| Acetone tail T2 | 1.0% |
| Acetone organic phase S1 | 11.0% |
| Acetone water phase S1 | 16.8% |
| $H_2O$ tail T2 | 5.1% |
| Cumene tail T2 | 12.6% |
| Cumene tail T3 | 12.9% |

Characteristics of end product

| | |
|---|---|
| Content of $H_2O$ | 250 ppm |
| Content of methanol | 49 ppm |
| Permanganate test (ASTM D1363) | 13 h |

Examples 1–6 were also carried out with a feeding consisting of streams of raw acetone, coming from an industrial plant, having the following characteristics:

| content of H₂O | 4.0%; |
|---|---|
| " of cumene | 8400 ppm; |
| " of methanol | 190 ppm |

The results obtained are analogous to those already indicated.

From these streams, using purification methods such as those used in present-day commercial plants, it is possible to obtain a product within specification having the following typical characteristics:

| Content of H₂O | 0.15–0.2% |
|---|---|
| " of methanol | 200–250 ppm |
| Permanganate test (ASTM D1363) | >3 |

We claim:

1. A process for the purification of acetone containing cumene, water, aldehydes and methanol as impurities, which comprises:

feeding a stream of acetone containing said impurities obtained from a process for the production of phenol and acetone coming from a primary fractionation of said process to a first distillation column and also feeding thereto a solution of sodium hydroxide;

withdrawing a stream at the bottom of the first column to remove polyaldehydes, water and methanol, withdrawing at the head of the first column, a stream consisting of acetone and water and cumene, and feeding said stream to a second column and also feeding thereto triethyleneglycol as an extractive solvent;

recovering substantially anhydrous acetone from the head of the second column;

feeding the bottom product of the second column, containing triethyleneglycol, water, cumene and acetone, to a third distillation column and recovering an azeotropic mixture of water and cumene from the head and anhydrous triethylene glycol from the bottom of said third column;

feeding the azeotropic mixture of water and cumene to a decanter and separating therein a water phase containing acetone and an organic phase containing cumene and acetone, and recycling said water phase containing acetone to said first column and feeding said organic phase to said primary fractionation.

2. The process according to claim 1, wherein said first column is operated at atmospheric pressure, with a reflux ratio of between 0.2 and 0.5, and a temperature at the bottom of from 102° to 110° C.

3. The process according to claim 1, wherein between 12% and 17% of acetone containing said impurities and a solution of about 2% sodium hydroxide are fed to said first column.

4. The process according to claim 1, wherein said second column is operated at atmospheric pressure, with a reflux ratio of between 0.5 and 1.5, and an autogenous temperature at the bottom.

5. The process according to claim 1, wherein the substantially anhydrous acetone recovered from the head of the second column has a water content of <300 ppm, and the bottom stream contains triethyleneglycol, water, cumene and about 3% acetone.

6. The process according to claim 1, wherein the amount of said stream from the head of the first column fed to the second column and contacted with triethyleneglycol is from 0.6 to 1 times the acetone containing said impurities fed to the first column.

7. The process according to claim 1, wherein the third column is operated at atmospheric pressure, with a reflux ratio of between 0.1 and 0.7 with respect to the acetone containing said impurities fed to the first column.

8. The process according to claim 1, wherein the anhydrous triethylene glycol recovered from the bottom of the third column is recycled to the second column.

* * * * *